United States Patent [19]
Milosevic

[11] Patent Number: 5,088,821
[45] Date of Patent: Feb. 18, 1992

[54] SPECTROSCOPIC ANALYSIS SYSTEM WITH REMOTE TERMINALS

[75] Inventor: Milan Milosevic, Fishkill, N.Y.
[73] Assignee: Nicolas J. Harrick, Ossining, N.Y.
[21] Appl. No.: 546,082
[22] Filed: Jun. 29, 1990
[51] Int. Cl.[5] .................. G01J 3/40; G01N 21/47; G01N 21/55
[52] U.S. Cl. .................. 356/319; 250/339; 356/51; 356/311; 356/346; 356/244; 356/445
[58] Field of Search .............. 356/300, 313, 317, 318, 356/319, 323, 325, 326, 328, 244, 346, 445, 446, 311; 250/338.1, 339

[56] References Cited

U.S. PATENT DOCUMENTS

| | | | |
|---|---|---|---|
| 3,672,774 | 6/1972 | Bojic et al. | 356/313 |
| 3,977,787 | 8/1976 | Fletcher et al. | 356/346 |
| 4,657,390 | 4/1987 | Doyle | 356/346 |
| 4,770,530 | 9/1988 | Van Aken et al. | 356/323 |
| 4,835,389 | 5/1989 | Doyle | 250/343 |

FOREIGN PATENT DOCUMENTS

| | | | |
|---|---|---|---|
| 2820910 | 11/1978 | Fed. Rep. of Germany | 356/445 |
| 3538626 | 4/1986 | Fed. Rep. of Germany | 356/319 |
| 24833 | 2/1983 | Japan | 356/445 |
| 95220 | 5/1986 | Japan | 356/244 |
| 2096347 | 10/1982 | United Kingdom | 356/319 |
| 2110836 | 6/1983 | United Kingdom | 356/319 |

OTHER PUBLICATIONS

Brimmer et al, Applied Spectroscopy, vol. 40, No. 2, Feb. 1986, pp. 258-265.

Primary Examiner—F. L. Evans

[57] ABSTRACT

A versatile optical analysis system comprising a spectrophotometer having a collimated radiation source, an output port for the radiation, an input port for external radiation, a detector, and means for processing electrical signals representative of radiation from a sample to be analyzed. The system also comprises one or more remote terminals where the sample is located, and novel radiation piping means for selectively piping radiation from the spectrophotometer to the remote terminal or vice versa. Novel remote terminals are also described for carrying out diffuse reflection, external reflection, or emission analysis.

30 Claims, 17 Drawing Sheets

SPECTROSCOPIC ANALYSIS SYSTEM WITH REMOTE TERMINALS

BACKGROUND OF THE INVENTION

This invention relates to spectrophotometer analysis systems comprising a spectrophotometer and terminals, remote from the spectrophotometer, where the sample to be analyzed is located.

Such systems conventionally comprise a conventional spectrophotometer which is provided with an optical port through which a radiation beam can be passed, either out from or into the spectrophotometer. Means are connected to the port to pipe the radiation out to or in from a remote sampling terminal where the sample is located.

SUMMARY OF THE INVENTION

An object of the invention is a system of the type described with improved radiation piping means which minimizes radiation attenuation.

A further object of the invention is a system of the type described with an improved radiation piping means that allows plural sampling terminals to be selectively optically connected to the piping means.

Another object of the invention is novel sampling terminals enabling the carrying out of spectral analysis using diffuse reflection, external reflection, emission, and other techniques.

These and other objects and advantages of the invention are achieved, in accordance with one aspect of the invention, by a versatile optical sampling system that is capable of performing infrared (IR) or other spectral spectroscopic analysis on remotely located samples which can be large or small. Specially designed sampling terminals, employing different spectroscopic techniques, are described as integrated components of the system. The sampling terminals may be located at some distance from the spectrophotometer and are connected to it via an optical transfer system designed for maximum optical efficiency. Each terminal may be located in a controlled atmosphere, in a glove box, and/or at strategic places along a process control line.

In one mode of operation in accordance with another aspect of the invention, the system allows the multiplexing of the spectrophotometer source radiation to one of two or more sampling terminals which contain a sample to be analyzed as well as a detector for the analyzing radiation. The amplified detector signal from the selected sampling terminal is switched to the spectrophotometer for further processing. In a second mode of operation for doing emission spectrophotometry, radiation from one of two or more sampling terminals may be directed back to the spectrometer detector. In either case, one spectrophotometer may be shared among several sampling areas and/or different spectral techniques.

In accordance with still another aspect of the invention, the optical transfer system described is capable of conducting IR or other radiation over long distances without introducing unacceptable energy loss or optical distortion. Since each sampling terminal in one mode is located outside the spectrophotometer and has its own detector, design restrictions which are present with internally mounted attachments are absent. The detector and optical configuration of each sampling terminal is completely integrated for enhanced performance.

BRIEF DESCRIPTION OF THE DRAWINGS

Other objects and advantages will be apparent from the detailed description that follows of several different embodiments of the invention, taken in conjunction with the accompanying drawings wherein.

DETAILED DESCRIPTION OF THE PREFERRED EMBODIMENTS

Figure 1:
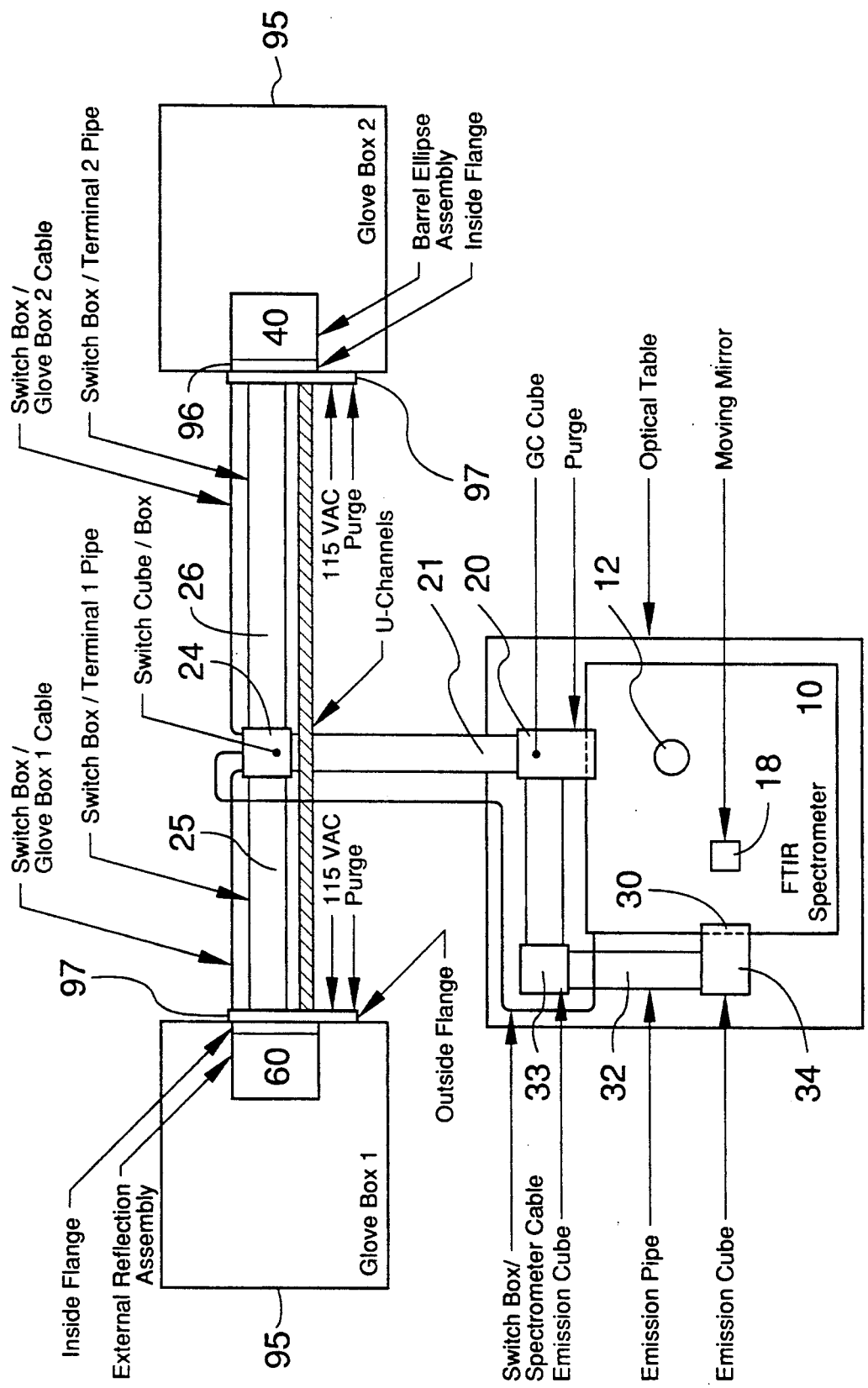
FIG. 1 is a block diagram of one form of spectral analysis system in accordance with the invention.

A block diagram of one configuration of a system according to the invention is shown in FIG. 1. For the sample analyses described later, a Bio-Rad Digilab FTS-40 Fourier Transform Infrared (FTIR) spectrophotometer 10 was used. The system of the invention is, however, compatible with any FTIR spectrometer equipment with an external collimated beam GC (an acronym for Gas Chromatograph) port and an external detector input. The spectrophotometer comprises a source of modulated radiation 12 which is formed into a collimated beam which exits the spectrophotometer at an optical port 13. It should be noted that the "collimated" radiation which exits any FTIR spectrophotometer is not perfectly collimated. Only light which originates from a theoretical point source with a zero area can be so collimated. In practice, the area from which light is collected is typically equivalent to a circle of 6 mm diameter. The IR light from this source 12 is collimated via a paraboloid mirror 14 as indicated in the typical source optics configuration of FIG. 2. Since an extended, rather than point, source is employed, the divergence of the beam is:

$$A_{max} = \tan^{-1} D_{max}/2f_{eff} \qquad (1)$$

where $A_{max}$ is the maximum angle of deviation from the collimated direction shown by the solid lines 16, $D_{max}$ is the diameter of the source, and $f_{eff}$ is the effective focal length of the parabolic mirror. For a typical case where $D_{max}$ is 6 mm and $f_{eff}$ is 152.4 mm (6 inches), $A_{max}$ is 1.1°. The beam from the mirror 14 (see FIG. 7) is passed through an aperture plate 17 and impinged upon a movable plane mirror 18. In one position of the mirror 18 (not shown in FIG. 7), the beam is directed to the output port 13 (FIG. 1). The latter is connected to a GC cube 20 which directs the exiting beam into a radiation pipe 21.

It will be appreciated that, for the example given, with a 1.1° divergence, a nominally collimated 50 mm diameter beam would spread to 126 mm after only 2 meters. In order to prevent this spreading of the IR beam, the optical transfer system in accordance with one feature of the invention uses nonmetallic tubing with an internal diameter large enough to accommodate the nominally collimated beam. For the 50 mm example given, an internal diameter of 53 mm is chosen. Reflections from the inside surface or wall of the nonmetallic tubing act to effectively contain the beam within the 53 mm diameter cross-section. The material for the tubing can be selected from among many non-metals, such as glass, ceramics, or plastics. Ceramics, such a porcelain, can be obtained with smooth, glossy surfaces of high reflectivity. Similarly, molded plastics, such as polyvinylchloride, can be obtained with similar reflecting surfaces. I prefer glass tubing. Commercial optical glass tubing typically comes with a smooth surface, which we have found causes a negligable amount of scattering. Also, since the angle of incidence of the IR beam on the walls of the tubing is typically 89 degrees or higher (i.e., grazing incidence), the reflectivity of the tubing is very high.

Figure 3:
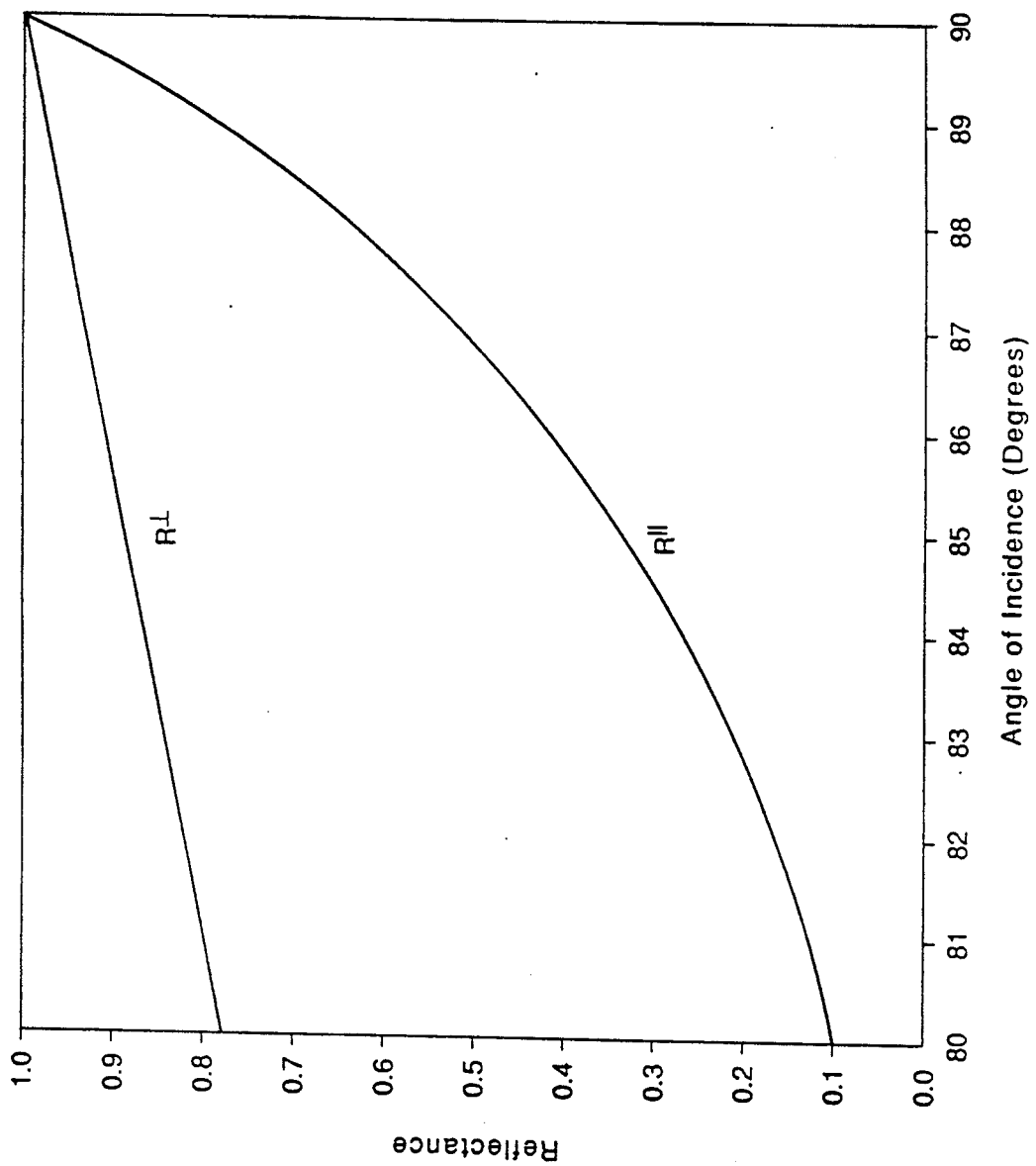
FIG. 3 shows reflectance curves for the parallel and perpendicularly polarized components of incident IR radiation on a polished glass surface for use as the piping medium in the system of FIG. 1.
Figure 4:
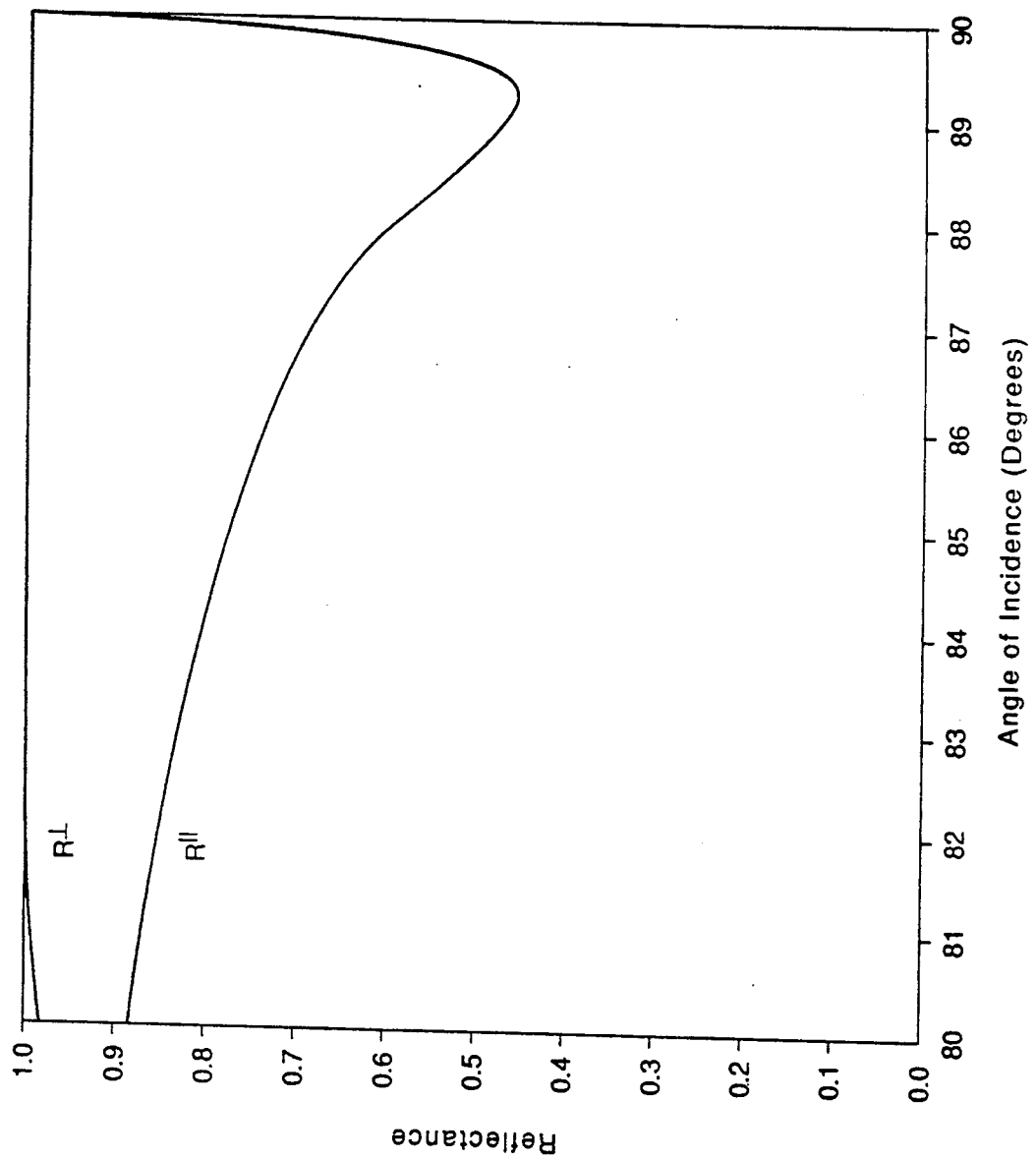
FIG. 4 shows, for comparison purposes, the reflectance curve of an aluminized surface.

This is illustrated in FIG. 3 for reflectance from polished glass for incident radiation of 10 µm wavelength. As will be noted, at grazing incidence, the reflectivity of the perpendicularly polarized beam component is about 95% or higher; for the parallel component it is over 80%. In comparison, metals, such as gold or aluminum, at such high angles of incidence would have a much lower reflectivity. This is shown in FIG. 4. While the reflectance of the perpendicular component for the metal remains high, the reflectance of the parallel component can fall below 50% at an angle of just above 89°.

Figure 2:
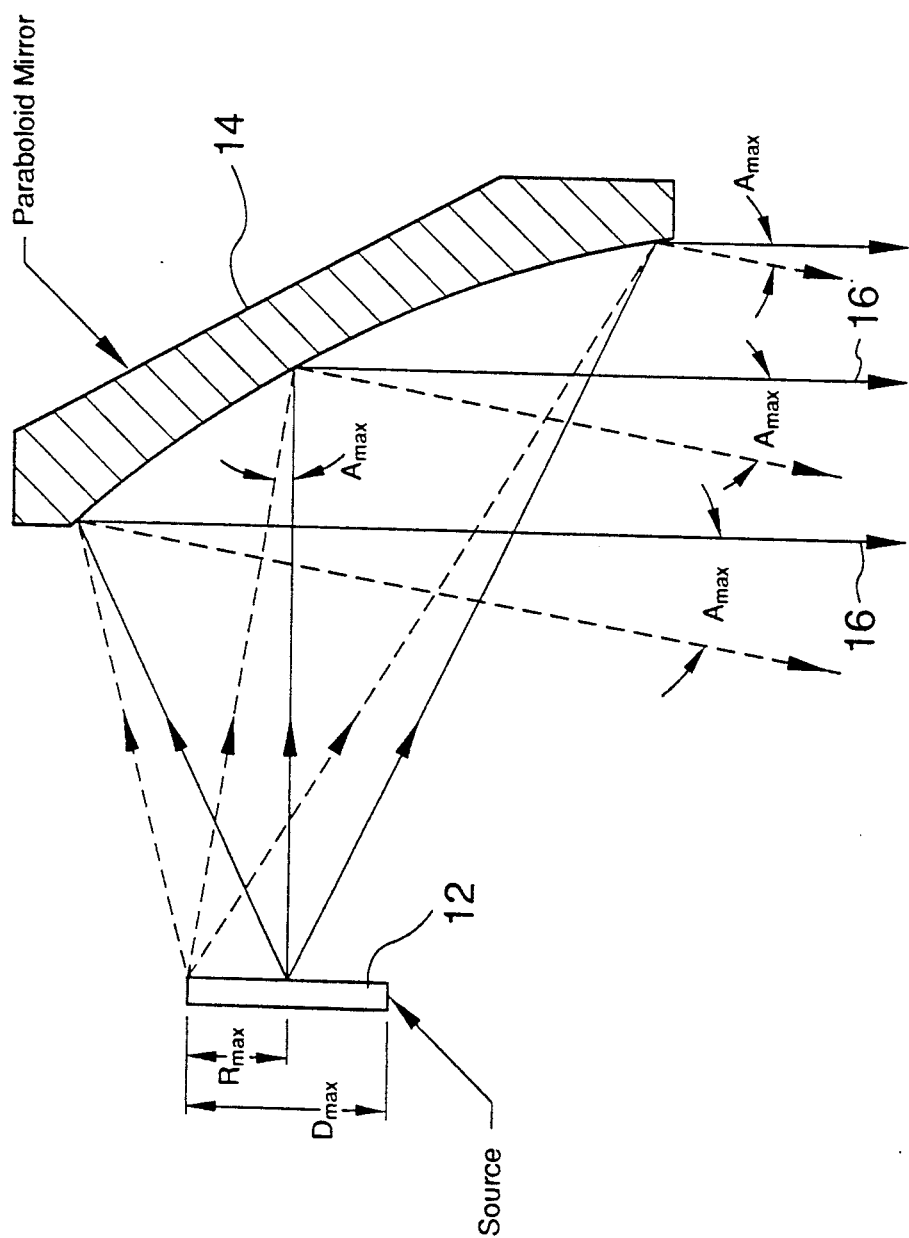
FIG. 2 depicts a source optics configuration for generating a collimated radiation beam for use in the system of FIG. 1.

One of the more important questions regarding the optical piping means or transfer line is how the intensity of the radiation changes along the length of the line. The first and most obvious cause of loss in the transfer line is light absorption by the host atmosphere or gas in the piping. This loss can be controlled by the introduction of a nonabsorbing host gas such as nitrogen, oxygen, or argon. An alternate, though somewhat less practical solution which would completely eliminate loss due to host gas absorption, would be to evacuate the transfer line. The second source of loss is due to reflection at the walls of the tubing. The analysis of the reflection loss requires an understanding of the divergence of the collimated beam coming from the spectrometer. There would be no reflection loss if the beam were perfectly collimated. Then the cross-section of the beam would not change with distance and radiation would never reflect off the walls of the tubing. The reflection loss occurs because the "collimated" radiation is not perfectly collimated, as illustrated in FIG. 2. Light coming from the focal point of the parabolic mirror is perfectly collimated. Light coming from other areas of the source is skewed at some angle. The skew angle, A, is related to the distance from the focal point, r, by $$\tan A = r/f_{eff} \qquad (2)$$

At the maximum distance from the focal point, r is the radius of the source, $R_{max}$, and $D_{max}/2$ may be substituted for r in the above relationship. After rearrangement, Equation (1) for maximum divergence, given earlier, results. In all cases of practical importance, $r << f_{eff}$. Therefore, A is a very small angle and tan A is approximately equal to A. It then follows that the light collected from a point on the source has a skew angle that depends on the distance of that point on the source from the focal point. Based on the above considerations, the distribution of the intensity of radiation per skew angle is $$I(A) = (2A/A^2)I_0 \qquad (3)$$

where $I_0$ is the total beam intensity.

Figure 15:
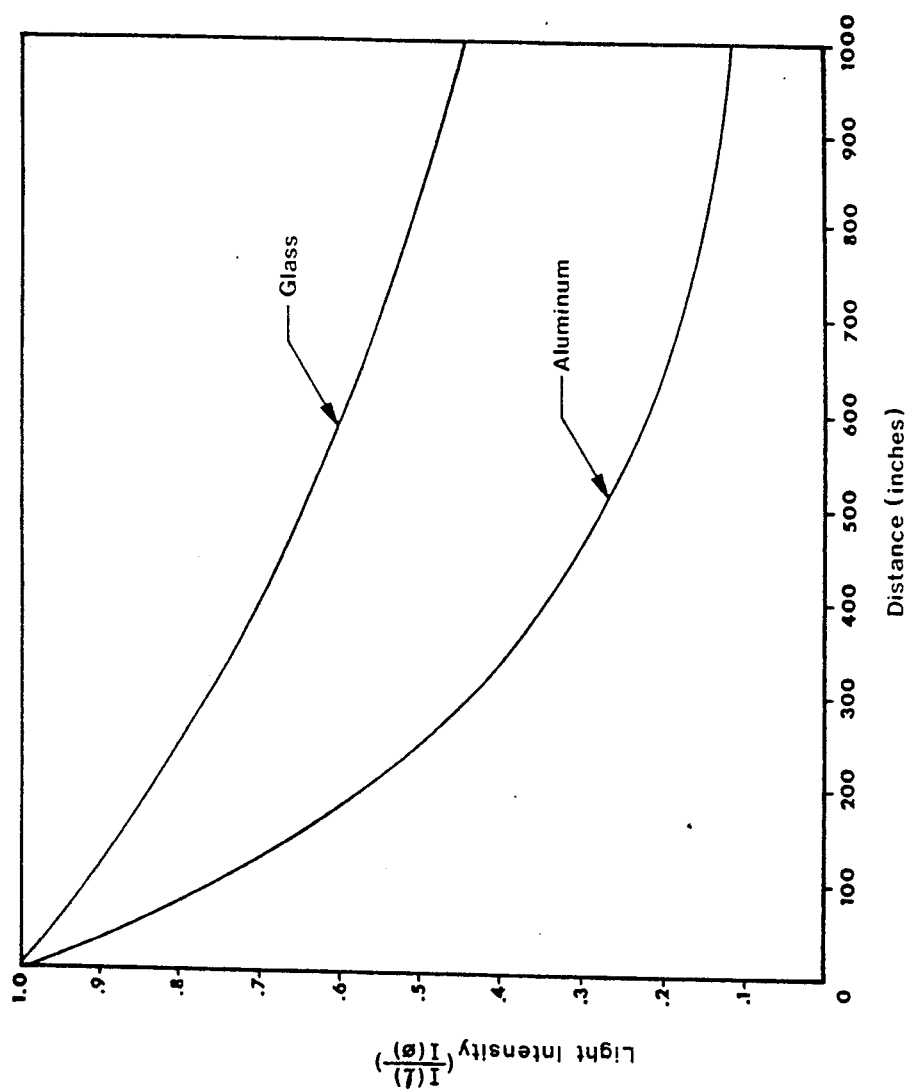
FIG. 15 is a graph comparing light intensity versus distance for two kinds of optical transfer lines.

It can be shown that the attenuation of the radiation with the path traversed depends on the skew angle A, and to obtain the relationship of the attenuation for the entire beam requires integration over all skew angles. These calculations resulted in the graphs of FIGS. 3 and 4, which can be accentuated by calculating light intensity as a function of distance for a two-inch optical transfer line. FIG. 15 shows the results, and clearly demonstrates the superiority of the polished glass light pipe compared with an aluminized light pipe. With such low attenuation associated with the light pipe of the invention, sampling terminals may be located tens of meters distant from the spectrometer. Furthermore the usable spectroscopic range is from the UV to the far infrared region of the spectrum. These characteristics compare very favorably with those of currently available state-of-the art IR fiber optics, whose use is limited to 10 µ wavelength.

Returning now to FIG. 1, the light piped up the light pipe 21 is incident on an electrically switchable cube 24, a commercially available component, which under control of electrical signals will direct the light either to the left along a polished glass left optical pipe 25 or to the right along a polished glass right optical pipe 26. The switch cube 24 essentially comprises a 45° mirror which can be pivoted into one of two or more positions to route the light in the direction desired. Connected at the remote end of each of the left 25 and right 26 optical pipes is a remote terminal in accordance with the invention.

The system can function in either of two basic modes: reflection/transmission or emission. To summarize briefly, in the first reflection/transmission mode, the spectrometer 10 provides a source of modulated collimated IR radiation. Detection is provided by the external sampling terminal. When using a spectrometer of the Digilab type, the automatic operation of the Digilab external port mirror is used to lower the mirror associated with the GC port 13. The beam can then exit the GC port 13. Also, the automatically operable external detector switch and external detector input of the Digilab instrument are used. Other spectrometers may require different adjustments. The source radiation is then routed, via the optical transfer system 20, 21, 24, 25, 26, to one of two or more remotely located sampling terminals, where the spectroscopic measurement is performed. Light which has interacted with the sample at the selected sampling terminal is then collected and condensed onto a local detector, where it is sensed. Placement of the detector is optimized with respect to the optical system. The resultant electrical signal is amplified by a preamplifier, which is also located within the sampling terminal. To minimize noise pickup, the preamplifier is located as close as possible to the detector. The amplified signal is then sent, via shielded BNC cabling, back to the spectrometer where it is further processed. An electrical switch allows segregation of the detector signal of the sampling terminal.

In the second (emission) mode, the optical transfer system allows radiation from the sample to be routed from the sampling terminal via the optical transfer system 20, 21, 24, 25, 26 back to the spectrometer. The detector of the spectrometer is now used to sense this radiation. A special emission interface, built into the spectrometer, is used to route light entering the emission port to the detector.

In a preferred embodiment, the optical transfer system consists of a set of pipes mounted in cubes which contain fixed or rotatable mirrors. All pipes preferably are of DURAN borosilicate glass (#8330; Schott, Inc.), with the exception of the relatively short emission pipe assembly, which may be of stainless steel. The cubes are made of Delrin plastic (DuPont Co.) or anodized aluminum. Other polished glass tubes can be substituted for the DURAN. The GC cube 20 contains an aluminum-coated 45° plane glass mirror which can be rotated 90°. In one position, the reflection/transmission mode is selected and the beam from the spectrometer GC port 13 is directed to a sampling terminal. In the other position, the emission mode is selected. In this latter mode, light from a sampling terminal is routed back to an emission port 30 of the spectrometer through two additional pipes 31, 32 and cubes 33, 34. Emission cube 33 contains a fixed aluminum-coated 45° plane glass mirror. Emission cube 34 contains either a fixed 90° off-axis paraboloid aluminum mirror for spectrometers that require a focussed beam for the emission port, or a 45° plane mirror for spectrometers that require a collimated beam at the emission port. Adjustable stops in the GC cube are provided for the extreme positions of mirror rotation. The switch cube assembly 24 contains an aluminum-coated 45° plane glass mirror which can be rotated 180°. In the reflection/transmission mode, the spectrometer source radiation can be sent to any of the two or more sampling terminals by rotating the mirror in the switch cube. In the emission mode, light emitted from either of the sampling terminals can be routed back to the spectrometer. As with the GC cube, adjustable stops are provided for the two proper positions of mirror rotation. In the configuration depicted in FIG. 1, the switch cube 24 is elevated above the spectrometer 10. Aluminum U-channels 36 are used to support the switch cube in this position.

As explained earlier, to reduce the attenuation, the system is purged. For this purpose, the optical transfer system is closed by 50 mm diameter×6 mm thick KBr windows located at the spectrometer GC 13 and emission 30 ports and in the inside flange assemblies of the sampling terminals (explained below). Each KBr window may be installed in a mount which, when mechanically attached to the port or flange, compresses an O-ring which is placed in the mount. The transfer system can then be independently purged via a port in the GC cube 20.

Figure 5:
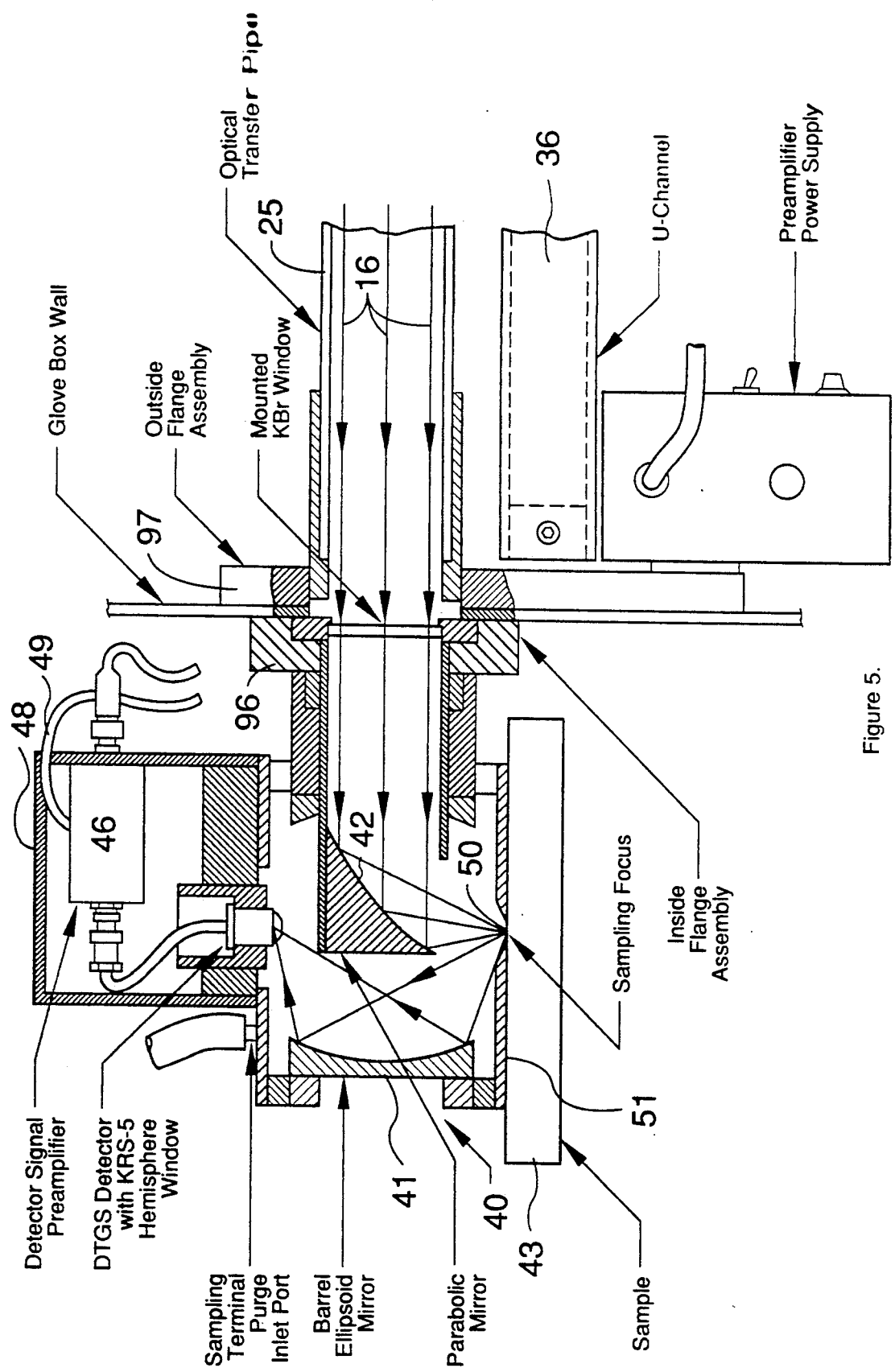
FIG. 5 is a view, partly in cross-section, of one form of sampling terminal in accordance with the invention for diffuse reflection analysis for use in the system of FIG. 1.

The individual sampling terminals are described below. One terminal in accordance with the invention may be referred to as a barrel ellipsoid terminal 40. This attachment is a multi-purpose sampling device for diffuse reflection, emission, and normal incidence specular reflection spectroscopy. It is illustrated in FIG. 5. The barrel ellipsoid sampling attachment consists of a large barrel-shaped ellipsoidal aluminum mirror 41 and a 99.25° off-axis parabolic aluminum mirror 42. The function of the parabolic mirror 42 is to focus the incident collimated beam 16 onto a sample 43. The focal point of the parabolic mirror 42 is also one of the focal points of the ellipsoid mirror 41. The function of the ellipsoid mirror 41 is to refocus reflected light from the sample onto a detector 45 as shown. Any commercially-available detector, such as Barnes Engineering Part No. 2-1162-83, can be used. With this particular detector, the geometry of the custom KRS-5 window, actually an integrating lens, has been designed to match the geometry of the ellipsoid mirror, thus maximizing the efficiency of light collected onto the active surface of the detector. The unamplified detected signal is then processed by a conventional preamplifier, for example, with a gain of 200, which is conveniently located within and shielded by the aluminum chassis 48 mounted on the barrel. The amplified signal is then routed by a cable 49 back to the spectrometer 10.

In the diffuse reflectance mode, the sample is illuminated at near normal incidence (which minimizes reflection losses) and redirects specularly reflected light back to the spectrometer source. The collection of specularly reflected light makes the barrel ellipsoid sampling terminal useful as a normal incidence specular reflection beam condenser attachment, provided that the reflected light is separated from incident light via a beam splitter. In its third function, the barrel ellipsoid 40 can serve as a collector of radiation emitted by a sample located at the sampling position. The barrel ellipsoid 40 terminal can be employed in either an upward or downward looking mode, whichever is preferable for a particular sample type. Furthermore, large samples may be examined due to the unrestricted area outside the sample focus. As will be observed, in use, any sample material is simply pressed against an orifice 50 in the side wall 51 of the terminal, exposing through the orifice 50 to the incident radiation the surface of the sample. The sample 43 in this case can act to seal off the system for purging.

Figure 6:
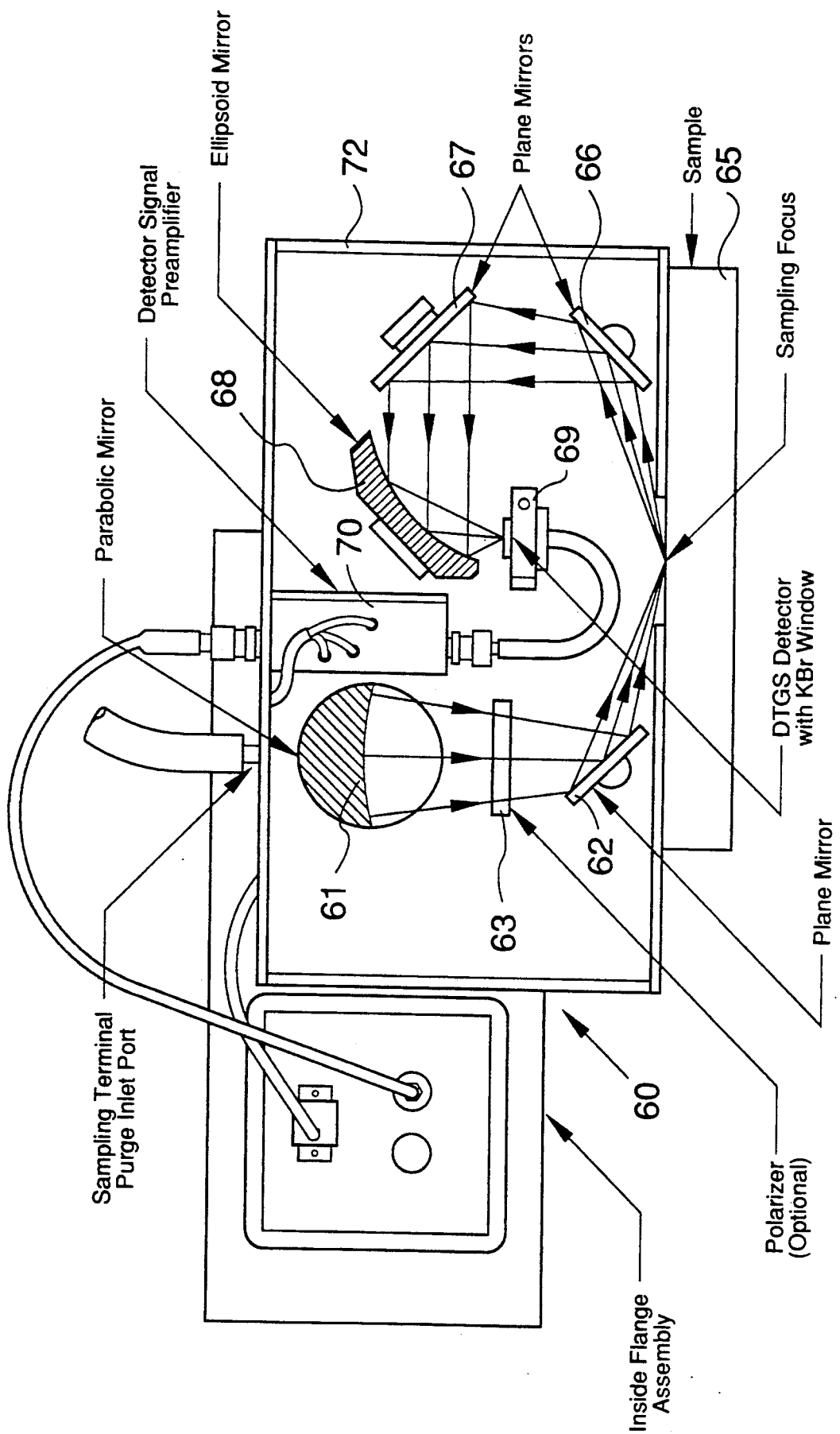
FIG. 6 is a view similar to FIG. 5 of another form of sampling terminal in accordance with the invention for external reflection analysis for use in the system of FIG. 1.

Another form of terminal in accordance with the invention may be referred to as a fixed angle external reflection terminal 60. This attachment 60 is a dedicated sampling device for the measurement of specular reflection at 75° angle of incidence. A diagram is given in FIG. 6. The transfer beam 16, not shown in this view, is directed onto a 90° off-axis aluminum paraboloid mirror 61. The beam is then reflected onto a plane first surface aluminum-coated glass mirror 62. Between the paraboloid and plane mirrors is a sample slide plate holder 63. An optional wire-grid polarizer may be inserted into this holder when studies of thin films on metal substrates are made. The beam from the mirror 62 then strikes the sample 65 at a 75° angle. The focal point is in the plane of the sample. Specular reflection from the sample is then reflected off two plane first surface aluminum-coated glass mirrors 66, 67 onto an aluminum ellipsoid mirror 68 which collects and refocusses the light onto a DTGS detector 69 (for example, from Barnes Engineering with a standard coated KBr window). As with the barrel ellipsoid terminal, the unamplified signal is processed by a preamplifier 70, which is conveniently located within and shielded by the aluminum terminal chassis 72. The amplified signal is then routed back to the spectrometer. As with the barrel ellipsoid embodiment of FIG. 5, the reflection terminal 60 shown in FIG. 6 has the advantages of being operable in upward or downward looking modes and of having an unrestricted sampling area.

Figure 7:
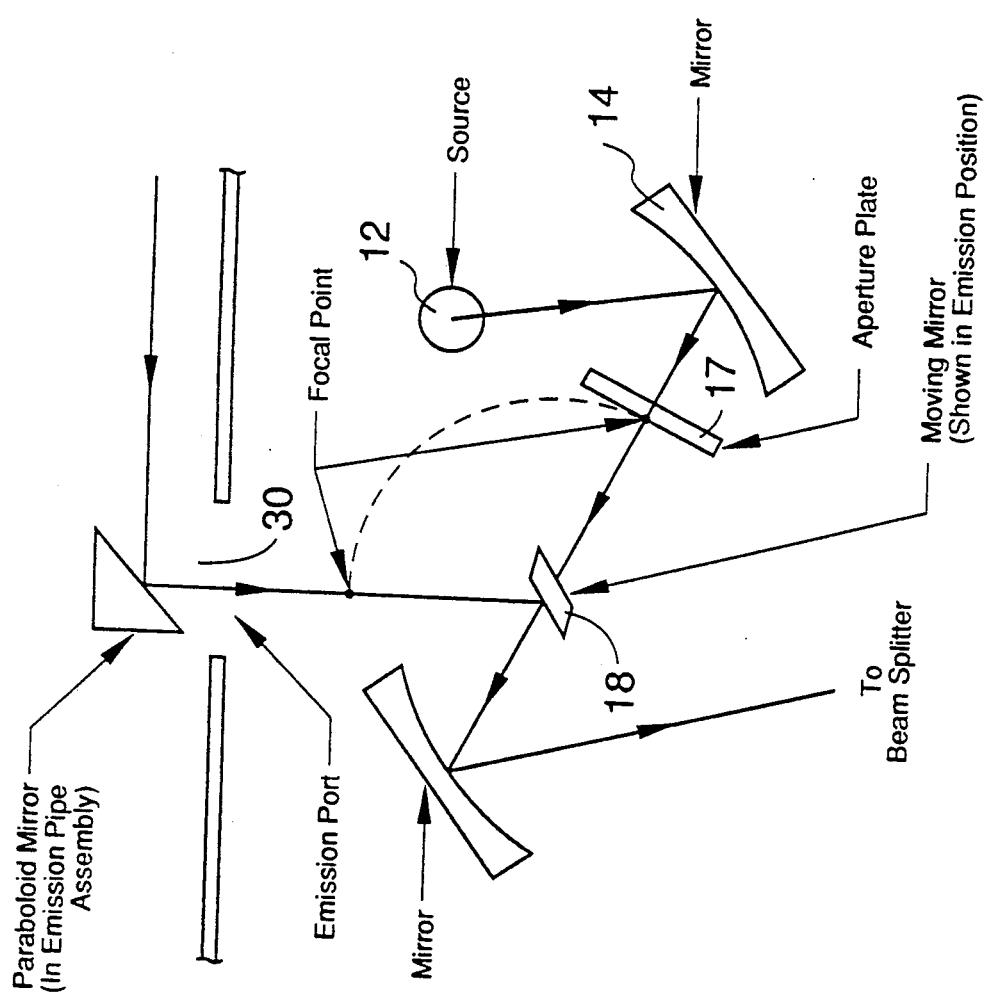
FIG. 7 is a schematic optical diagram illustrating the optical path for interfacing one form of sampling terminal in accordance with the invention for doing emission spectrophotometry in a system of the type illustrated in FIG. 1.

The emission interface assembly, which is mounted internally on the aperture plate of the Digilab instrument, is illustrated in FIG. 7. This assembly is an electro-mechanical device which allows two modes of operation. In the first, the sample beam is uninterrupted and the spectrometer may be used as a stand alone instrument. In the second, used by the system of the invention in the emission mode, the mirror 18 is moved into position so that only light which enters the emission port 30 of the spectrometer can strike the instrument detector. A low current/low voltage geared DC motor can be used to move the mirror 18 to either the emission or non-emission position. Changing direction on the motor is accomplished by reversing the polarity of the input switch via a DPDT switch accessed outside the instrument. The digital +5V supply of the Digilab instrument can be used as the power source for the motor. It will be understood that with other spectrometers, a different interface may be required.

Data were taken of various samples to determine the merits of the system. All data were taken with a Bio-Rad Digilab FTS-40 FTIR spectrometer with an SPC 3200 data station. All spectra were taken in the 4000–400 cm$^{-1}$ range with 8 cm$^{-1}$ resolution. For non-emission data, the external detector mode of the instrument was chosen and the emission interface assembly was switched to the non-emission mode. For emission data, the internal detector mode of the instrument was chosen. This latter mode selects the internal DTGS detector of the spectrometer. Also, for this latter mode, the emission interface assembly was switched to the emission mode. Filtered air (reduced water vapor and carbon dioxide) was used to purge the optical transfer lines, the sampling terminal, and the instrument.

Figure 8:
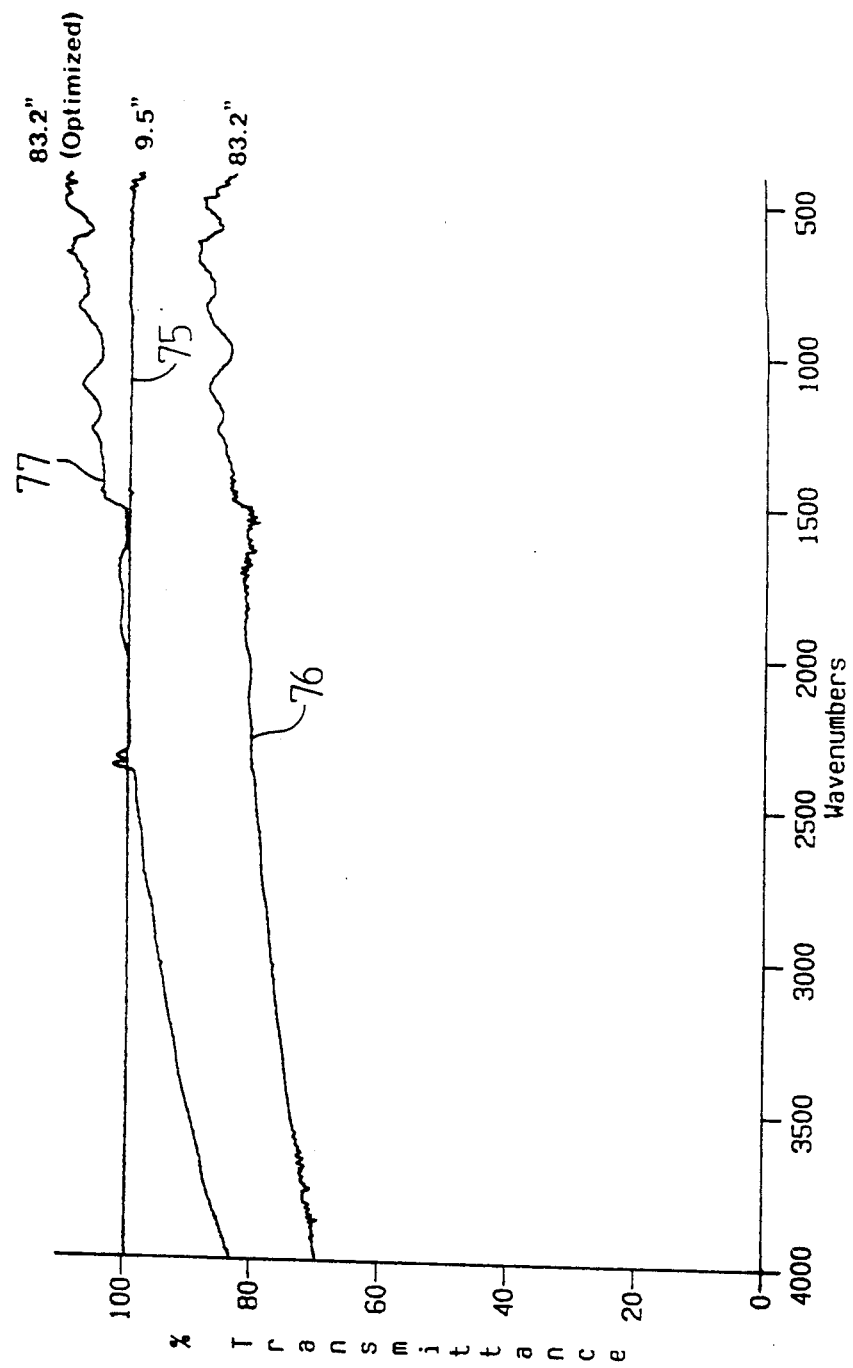
FIG. 8 shows transmittance curves indicating the radiation attenuation with increased lengths of the piping means.

Tests were first conducted to determine the attenuation of source radiation as a function of light pipe length. For the purposes of these tests, the source beam of the spectrometer was routed to the external reflection sampling terminal 60 without intervening mirrors. The optional wire-grid polarizer was not installed in the terminal. A plane aluminum-coated first surface glass mirror was used as the sample in the sampling terminal 60. The background spectrum was taken with this same sample in place for the shortest length possible between the spectrometer and the sampling terminal (9.5 inches). The standard bulkhead mounting hardware, including the previously described KBr window, was mounted on the GC port of the spectrometer. Between this hardware and the sampling terminal were a purged Delrin cube, the outside flange assembly, and the inside flange assembly. The center burst amplitude of the interferogram was recorded at −5.0 V. A sample spectrum, shown in FIG. 8 at 75, was then taken. The optical transfer line was then extended by 73.7 inches, using two joined glass pipes, for a total distance between the spectrometer and sampling terminal of 83.2 inches. The center burst amplitude of the interferogram was recorded at −4.0 V. The sample spectrum is shown in FIG. 8 at 76. With this last configuration, further alignment increased the optical throughput so that a center burst amplitude of −5.0 V was obtained. The repeat sample spectrum which was subsequently taken is also shown in FIG. 8 at 77. These tests and spectra suggest that, at the relatively short distances used, optical alignment has a much more significant effect on source intensity attenuation than the transfer distance. This finding is in agreement with theory. Also, those spectral characteristics seen in the 1200 to 500 cm$^{-1}$ region are in agreement with expectations for DURAN glass, when comparisons are made with the manufacturer's literature.

Using then the barrel ellipsoid terminal 40, a diffuse reflectance test was conducted using the same configuration described for the optical transfer tests in which the source radiation was transferred a total distance of 83.2 inches from the spectrometer 10 to the sampling terminal 40. A background spectrum was taken, using a piece of sandblasted aluminum as the reference. A sample spectrum was then taken of a 2.5 micron thick Mylar film over the same piece of sandblasted aluminum. The latter spectrum is given in FIG. 9.

An emission test was conducted with the same terminal 40, using the same system configuration shown in FIG. 1, with the following exceptions: the sampling terminal 40 was attached to the GC/switch pipe assembly through a compatable Delrin adaptor stand, and the sampling terminal was mounted in an inverted position. The GC/switch pipe assembly had a length of approximately 14 inches. For emission, the internal detector of the sampling terminal (and related preamplifier and power supply) are not used. Instead, as previously discussed, light emitted from the sample is routed directly back to the detector of the spectrometer 10. A special emission sampling block was used to heat the sample. This consisted of a 2.5 inch long by 2.5 inch wide by 0.5 inch thick aluminum plate with one side having a polished mirror surface. Inserted in this block are two ⅛ inch diameter 15 W heaters and an iron-Constantin thermocouple for temperature detection. The heaters and thermocouple were interfaced to a Harrick Scientific Analog Automatic Temperature Controller. Using this temperature controller, the sampling block was maintained at 57+/−1° C. All spectra were taken from 2000 to 400 cm$^{-1}$. One-half of the polished surface of the sampling block was painted with Krylon #1613 Semi-Flat Black enamel. The background spectrum was taken using this side of the block as the sample. A 2.5 micron thick piece of Mylar film was then placed on the unpainted polished side of the sampling block. The spectrum that was subsequently obtained is shown in FIG. 10.

Using the external reflection terminal 60, a 75° fixed angle reflection test was conducted using the same configuration described for the optical transfer test, in which the source radiation was transferred a total distance of 83.2 inches from the spectrometer 10 to the sampling terminal 60. A wire-grid polarizer was installed in the holder 63. A background spectrum was taken, using a plane first surface aluminum-coated glass mirror as the sample. A spectrum was then taken of a 500 Angstrom $SiO_2$ film over a first surface aluminum mirror. This spectrum is shown in FIG. 11.

Figure 9:
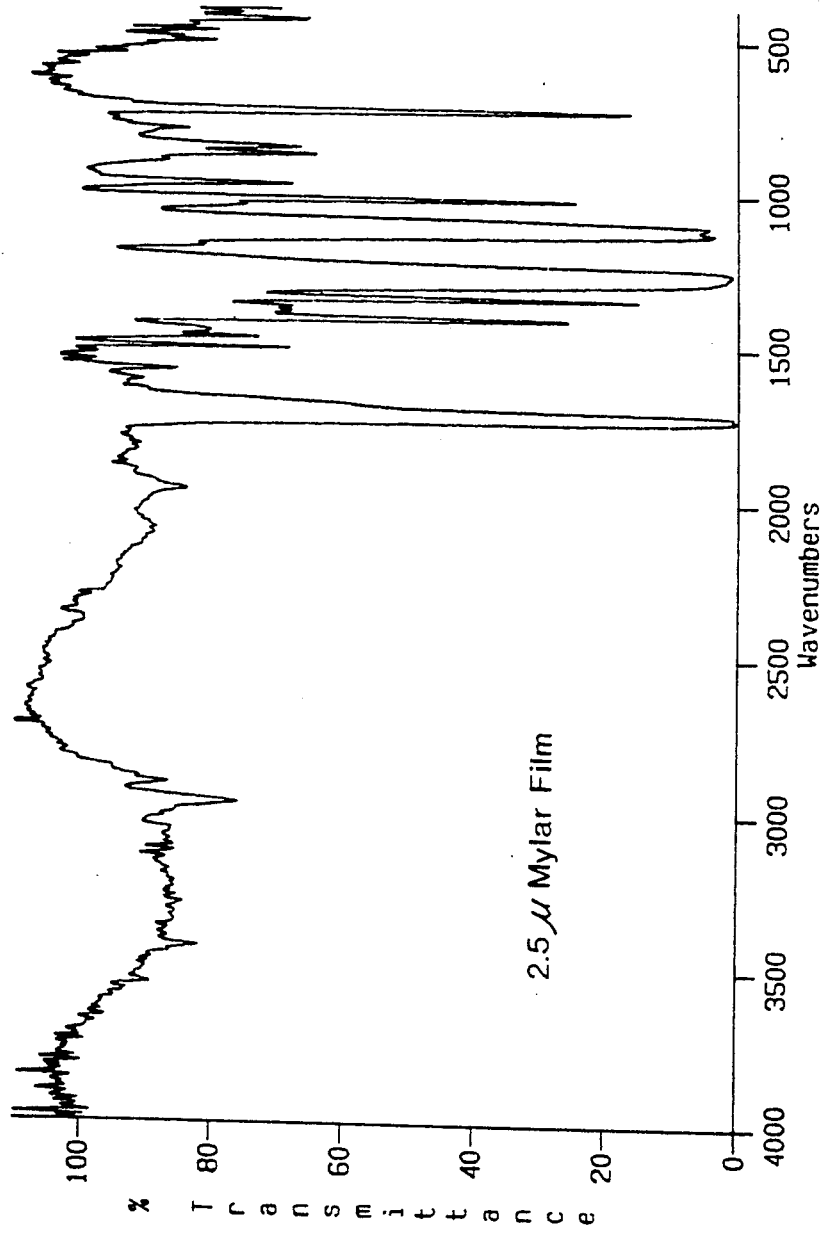
FIG. 9 shows a diffuse reflectance spectrum taken of a sample in the sampling terminal of FIG. 5 in a system of the type illustrated in FIG. 1.
Figure 10:
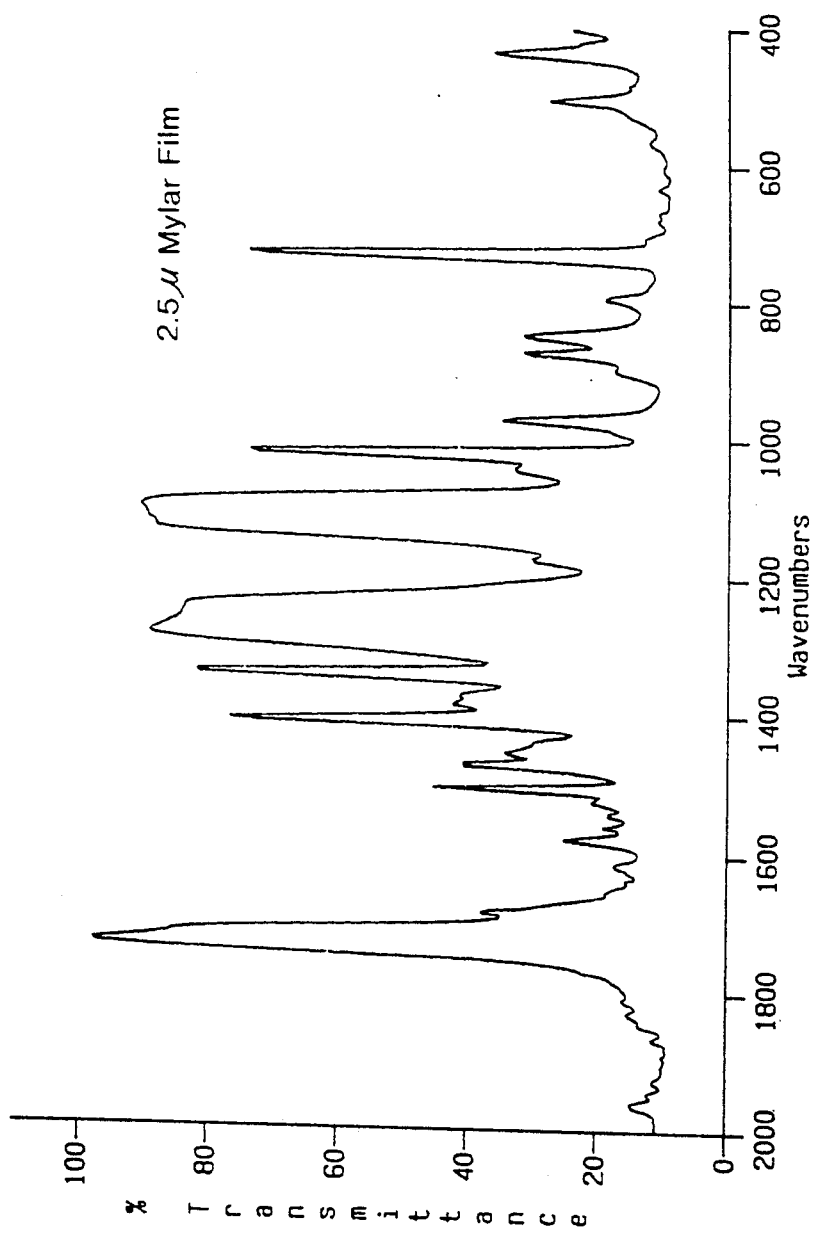
FIG. 10 shows an emission spectrum taken of a sample in the sampling terminal of FIG. 15 in a system of the type illustrated in FIG. 1.
Figure 11:
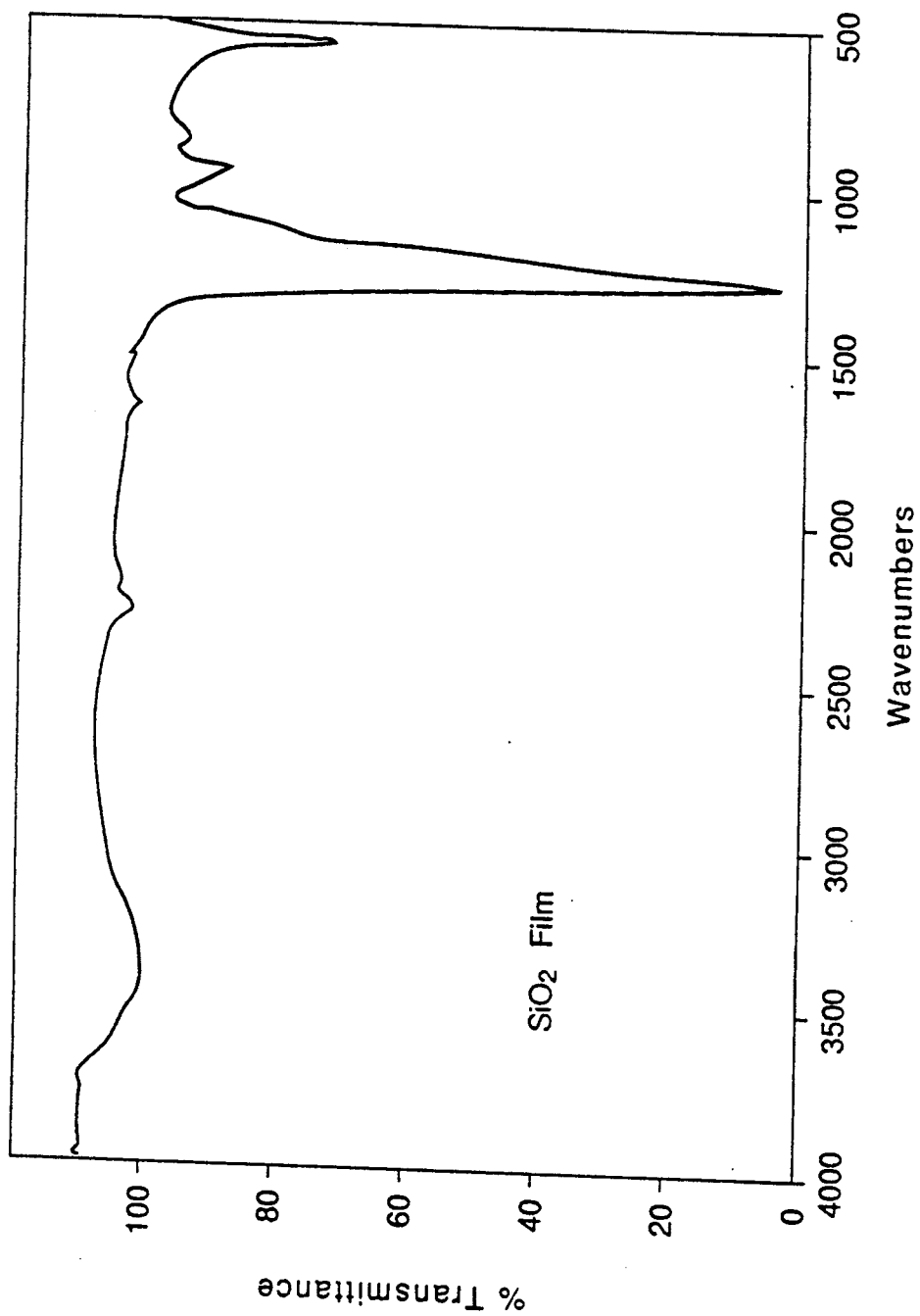
FIG. 11 shows an external reflection spectrum taken of a sample in the sampling terminal of FIG. 6 in a system of the type illustrated in FIG. 1.

It is evident from the spectra of FIGS. 9-11 that the system produced excellent results, even though the sampling terminals were located nearly seven feet away from the spectrometer itself. Moreover, the ability to multiplex the spectrometer to several different sampling terminals greatly enhances the versatility of the FTIR instrument. The long distances allowed by the optical transfer system permit sampling terminals to be located in hazardous areas or locations which would otherwise prove difficult. The ability of the system to operate in either a non-emission or emission mode and the ability of the sampling terminals to handle large samples are two additional distinct advantages.

Figure 12:
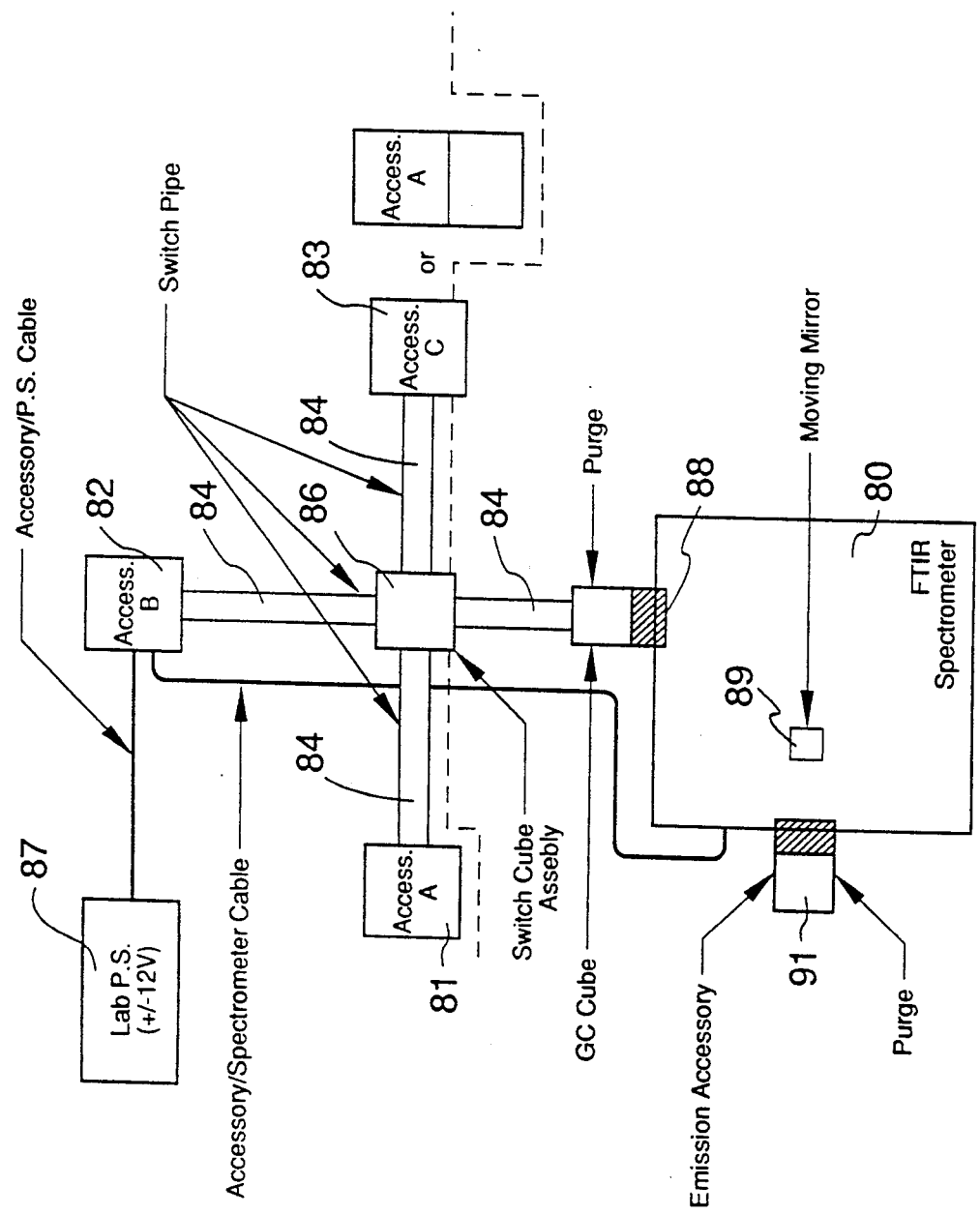
FIG. 12 is a block diagram of a system in accordance with the invention for use in a laboratory.

A block diagram of an alternative configuration of the system of the invention is given in FIG. 12. Any commercially available FTIR spectrometer 80 can be used. As with the previously described configuration, this system can also function in either of two basic modes; reflection/transmission or emission. In the first reflection/transmission mode, the spectrometer source radiation is transferred to one of three sampling terminals 81, 82, 83 via optical pipes 84 and through fixed and rotatable plane aluminum mirrors located in a switch cube assembly 86 interconnecting the four light pipes 84. Detection is provided by the external sampling terminal. A regulated +/−12V laboratory power supply 87 is used to supply power to the detector preamplifier located in each terminal. The signal cable to the spectrometer is manually connected to the accessory to be used. The collimated source beam can exit the GC port.

Figure 13:
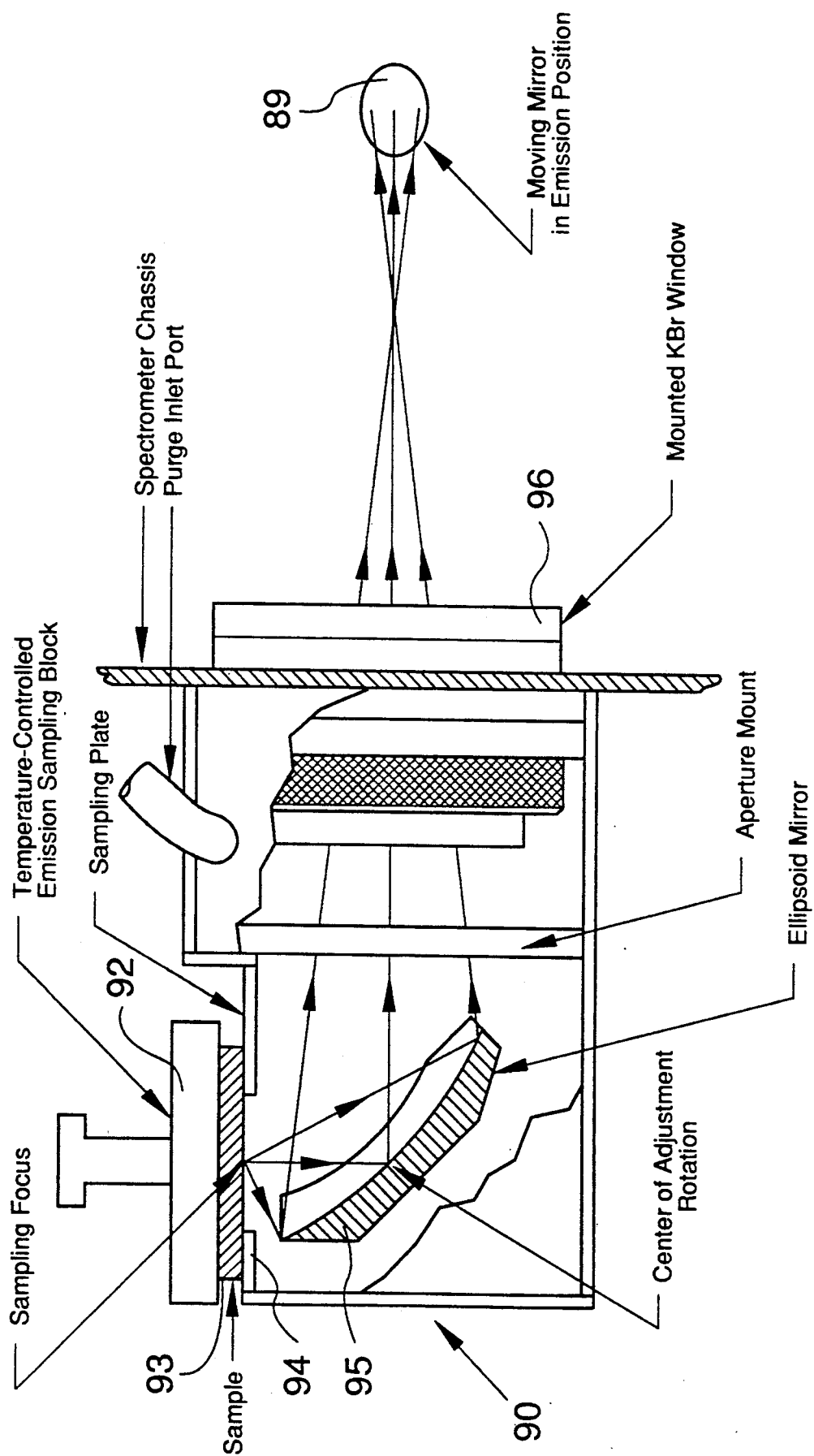
FIG. 13 is a view, partly in cross-section, of one form of emission sampling terminal in accordance with the invention for use in a system of the type illustrated in FIGS. 1 and 11.

In the emission mode, light from a dedicated emission sampling terminal 90 is routed to the spectrometer detector via emission access 91. A preferred embodiment of this terminal, shown in FIG. 13, is mounted directly to the emission port 91 of the spectrometer. Although shown in the upward-looking position, the terminal 90 may also be mounted in a downward-or sideways-looking position, to allow maximum versatility in the sampling configuration. The optical configuration of the dedicated emission terminal is relatively simple. A temperature controlled emission sampling block 92 holds a sample 93 against an opening in the sampling plate which constitutes a wall 94 of the terminal 90. Light emitted from the sample strikes a 90° off-axis parabolic or ellipsoidal mirror 95. This mirror can be rotated to maximize throughput. The emitted light is then routed through the optical system of the spectrometer to the detector of the instrument. As with the previously described sampling terminals, the sampling point of the dedicated emission terminal is in the plane of the outside of the chassis. This allows relatively large samples to be analyzed. The design, however, also allows easy mechanical substitution of the sampling plate for convenient repeatable measurements with, for example, a Harrick Scientific temperature-controlled environmental chamber. As with the other sampling terminals described, the dedicated emission terminal is separately purgeable and isolated from the rest of the system by means of a KBr window 96.

Figure 14:
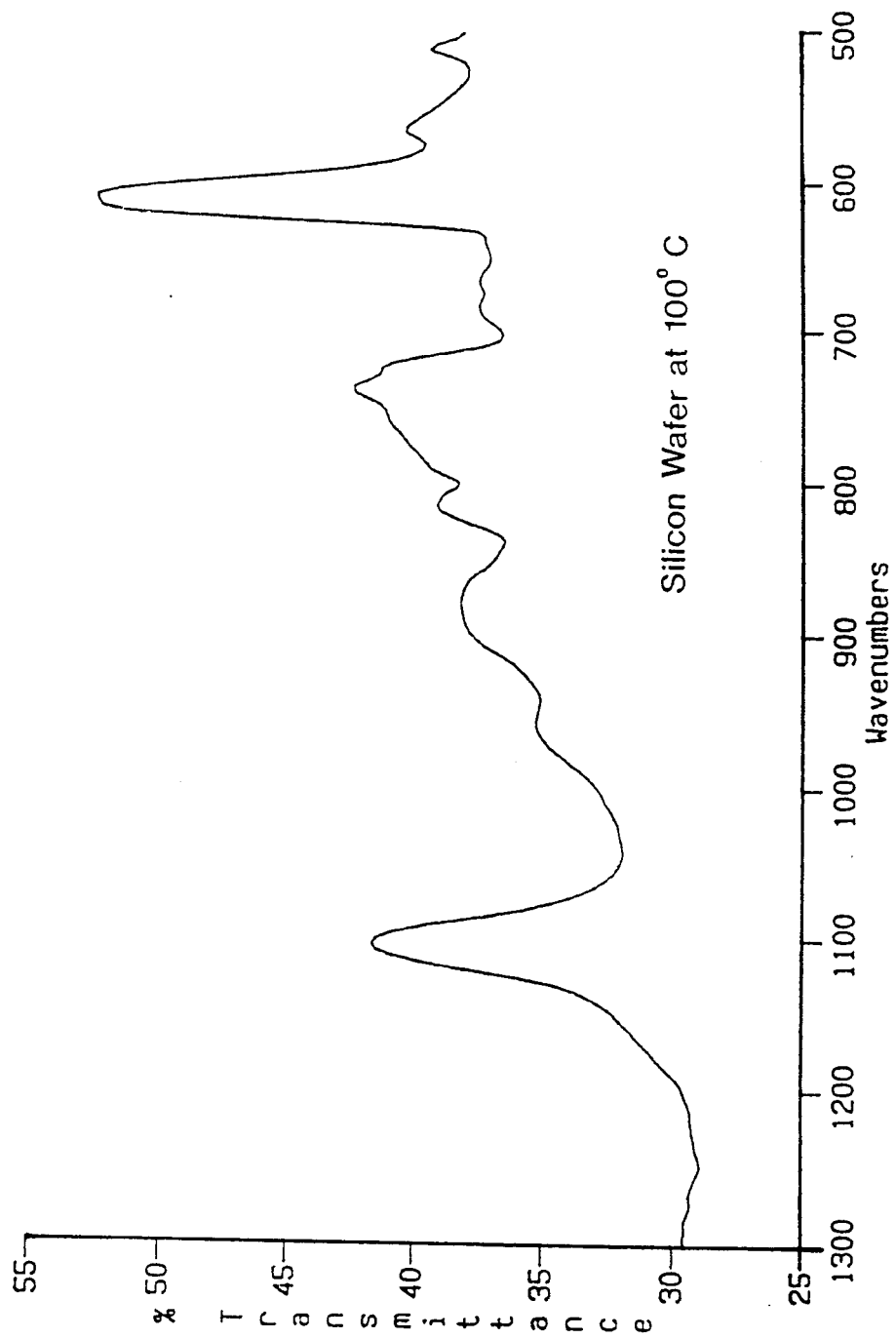
FIG. 14 is an emission spectrum taken of a sample in a terminal of the type illustrated in FIG. 12 in a system of the type illustrated in FIG. 1.

FIG. 14 shows the spectrum of a silicon wafer sample taken with the dedicated emission terminal of FIG. 13. The sample had only one polished surface. The spectrum was taken at 100+/−2° C., using two 35 W heaters in the emission sampling block. Again, the excellence of the spectrum should be noted.

A standard mechanical mounting configuration can be used for all sampling terminals. An example, which is not to be deemed limiting, is as follows. It can consist of a stainless steel tube, which also holds the first parabolic mirror, whose end projects outside the back of the housing by approximately one-half inch. On either side of this tube projection is a captively held bolt. The sampling terminal then mounts on a mechanically compatible flange assembly which provides the optical port and tapped holes for the terminal. The flange assembly also contains a mounted 50 mm diameter ×6 mm thick KBr window in the optical port for purge sealing of the optical transfer system. Also provided in this assembly can be sealed bulkhead connectors for the terminal purge, preamplifier power supply and preamplified detector signal. The inside flange assembly (shown at 96 in FIG. 1) is, in turn, mounted to the inside wall of a glove box (shown at 95 in FIG. 1) with RTV gasket sealing between the surfaces of the wall and flange. Note that this configuration not only isolates the optical transfer system atmosphere from other parts of the system, but also maintains the seal of the glove box with respect to the outside. Mounted to the inside flange assembly on the outside of the glove box (via access holes in the glove box wall) is the outside flange assembly 97. This provides an access hole for the light transfer pipe 25, 26, a mounting block for attaching the two previously discussed aluminum U-channels 36 (used to support the elevated switch cube 24), and an access hole for bulkhead connectors of the inside flange assembly. Also mounted to the outside flange assembly is the preamplifier power supply (not shown) which incorporates a modular commercially available +/−12VDC regulated unit. The configuration provides a universal mount, which allows different sampling terminals (designed for different spectroscopic techniques) to be plugged in at each sampling station. Optical, mechanical, and electronic compatibility are readily maintained between different terminals to allow this.

Figure 16A:
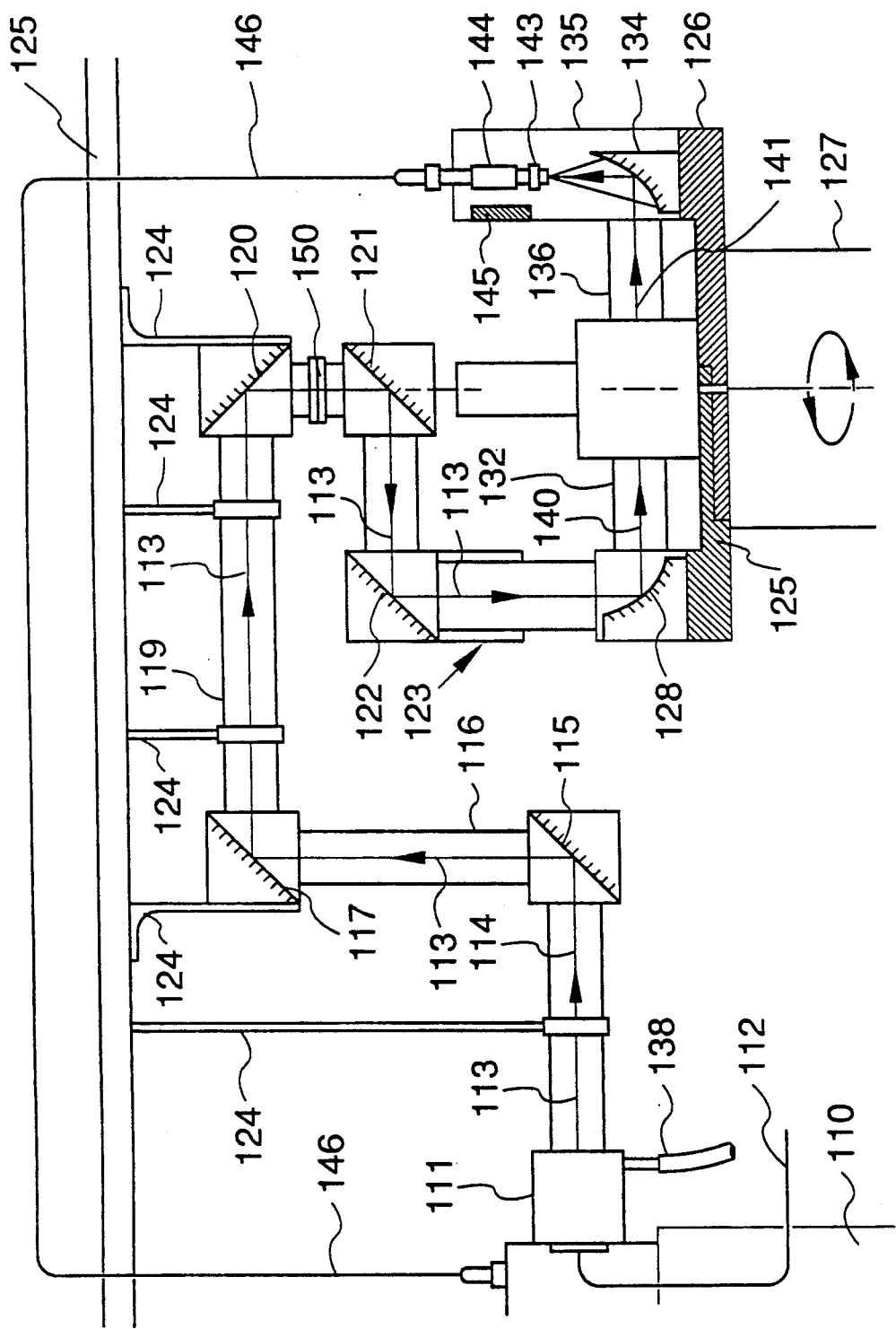
FIGS. 16A and 16B are, respectively, a view, partly schematic, of one form of variable angle reflection terminal in accordance with the invention shown connected to a system of the invention, and a top schematic view of some optical paths within the terminal.
Figure 16B:
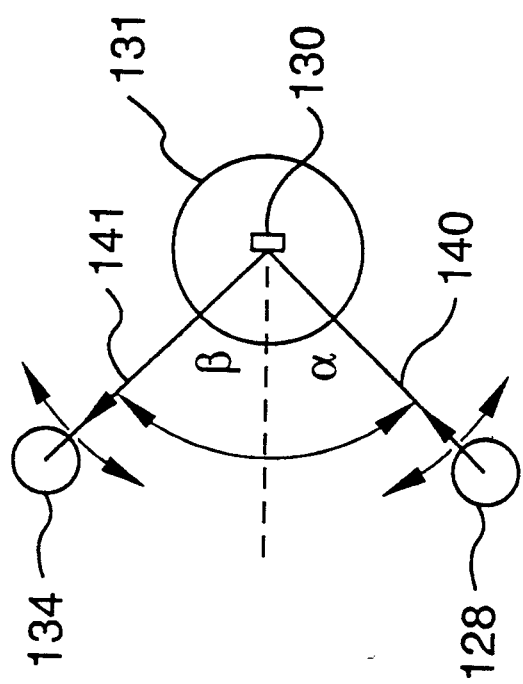

The operation of the system is not limited to the terminals so far described. Other kinds of remote terminals to do other kinds of optical analysis can be added to the system or substituted for the terminals illustrated. Examples are transmission terminals, internal reflection terminals equipped with a single or multiple reflection internal reflection element (ATR), a multiple unipoint grazing angle external reflection terminal, or a variable angle (external, internal, absolute) reflection/transmission/bidrectional terminal. The latter is illustrated in FIGS. 16A and 16B.

The spectrometer 110, which may be of any FTIR type, similar to that shown in FIG. 1, has a GC part 111 closed off by a KBr window 112. The radiation beam 113 from the spectrometer is piped along a hollow glass tube 114, reflected upwardly from a first planar mirror 115 via another glass pipe 116 to a second planar mirror 117, thence piped along still another glass pipe 119 to a third planar mirror 120, from which it reflects downward to a fourth planar mirror 121, thence sideways to a fifth planar mirror 122 mounted at one end of a telescoping tubing 123, which may also be of glass or other non-metallic material in accordance with the invention. The various radiation piping components are conveniently supported by suitable supports 124 as shown from a channel support 125 mounted above or suspended from a ceiling.

The telescoping tubing 123 is mounted on a first arm 125 which is rotatably mounted on a second arm 126 which in turn is rotatably mounted on a pedestal support 127. At the bottom of the telescopic tubing is seated a parabolic mirror 128 which focuses the collimated radiation beam 113 onto the surface of a fixed sample 130 seated within a Dewar chamber 131, one of whose ports is coupled via a pipe 132 to the telescoping tubing 123. The Dewar chamber is fixedly mounted on the support 127. The telescopic tubing 123 allows the vertical height between the two mirrors 122 and 128 to be varied to adjust for any small height mismatching of the system.

On the second rotatable arm 126 is mounted an ellipsoid mirror 134 inside a vessel 135 connected by a light pipe 136 to another port of the Dewar vessel 131. As will be observed, the entire optical system can be isolated from the atmosphere and thus suitably purged as schematically illustrated by a vacuum or gas line 138.

The optical paths, looking downward on the sample, are illustrated in FIG. 16B, with the focussed radiation 140 incident at an angle of incidence α on the vertically supported sample 130, from which reflected radiation 141 is created at an angle of reflection β. The ellipsoid mirror 134 collects the reflected radiation 141 and focusses it onto a detector 143. The resultant electrical signals are pre-amplified 144—these units may be powered by a local power supply 145—and returned by a cable 146 for processing to the spectrometer 110.

Both arms 125, 126 can be independently rotated about the axis of the sample 130 or Dewar 131 allowing continuous change of either or both incidence and reflection angles by the user. The terminal as shown in general purpose, capable of many different kinds of measurements. Also different ambient chambers, such as high temperature, can be substituted for the Dewar chamber.

The terminal illustrated is very versatile. A rotatable coupling 150 can connect the boxes housing mirrors 121 and 121, with the boxes housing mirrors 121, 122 and 128 rigidly connected together and supported on the first arm 125. Thus rotating arm 125, which rotates mirror 121, allows light to be sent in any direction perpendicular to the vertical axis of rotation of the system and toward mirror 122, and can thus vary over a wide angle of incidence the radiation on the sample through which the same axis passes. This construction allows many different spectroscopic techniques to be employed and also large samples to be measured.

In the detailed description, from time to time, reference was made to certain kinds of reflecting surfaces for the various mirrors described. It will be understood that this is not limiting, and other reflecting surfaces and materials can be readily substituted if desired.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An optical spectroscopic system comprising:
   a. a spectrophotometer having a source of modulated collimated radiation, means for directing the collimated radiation to an output port, and means for processing electrical signals representing the interaction of the radiation with a sample to be analyzed;
   b. at least one remote terminal spaced from the spectrophotometer and having an input port for receiving collimated radiation, means for supporting the sample to be analyzed, and a detector for receiving radiation after interaction with the sample;
   c. means for piping the collimated radiation from the output port of the spectrophotometer to the input port of the remote terminal, said piping means comprising hollow non-metallic tubing having a smooth interior surface;
   d. means for electrically connecting the detector to the spectrophotometer processing means.

2. The spectroscopic system of claim 1, wherein the hollow non-metallic tubing is glass and is configured and positioned relative to the outlet port such that the collimated radiation is incident on the glass interior surface at grazing incidence.

3. The spectroscopic system of claim 1, further comprising plural spaced remote terminals, said piping means comprising a first piping section, an optical switch box connected to the first piping section and having plural outlet ports, a second piping section connected between one of the switch box outlet ports and an inlet port of one of the remote terminals, a third piping section connected between another of the switch box outlet ports and an inlet port of another of the remote terminals, said optical switch box comprising means for selectively directing the radiation beam from the first piping section to any of the switch box outlet ports.

4. The spectroscopic system of claim 3, wherein the selective directing means of the switch box comprises a plane mirror and means for flipping the mirror to at least two positions.

5. The spectroscopic system of claim 1, wherein the remote terminal comprises means for focussing the collimated radiation onto the sample.

6. The spectrocopic system of claim 5, wherein the remote terminal comprises means for collecting reflected radiation from the sample and focussing same onto the detector.

7. The spectroscopic system of claim 1, further comprising means for enclosing the regions within the spectrophotometer, the piping means, and the remote terminal through which the radiation passes, means for purging the enclosing regions to provide a low radiation-absorbing atmosphere.

8. An optical spectroscopic system comprising:
   a. a spectrophotometer having a detector for modulated radiation, means for processing electrical signals representing the interaction of radiation with a sample to be analyzed, and an input port for receiving radiation;
   b. at least one remote terminal spaced from the spectrophotometer and having an output port for transmitting radiation, means for supporting a sample to be analyzed, means for controlling the temperature of the sample, and means for collecting radiation emitted by the sample and directing it toward the output port;

c. means for piping the radiation from the output port of the terminal to the input port of the spectrophometer, said piping means comprising hollow nonmetallic tubing having a smooth interior surface;

d. means for directing the radiation received from the input port to the detector.

9. The system of claim 8, further comprising another remote terminal connected to the piping means, said other remote terminal being configured to carry out reflection or transmission measurements.

10. The system of claim 9, further comprising a radiation source in the spectrophotometer, and means for selectively directing radiation from the source to the piping means or from the piping means to the detector.

11. The system of claim 8, wherein the nonmetallic tubing is of glass.

12. A remote sampling terminal for spectral analysis, comprising:
 a. means for supporting a sample to be analyzed,
 b. first optical means for receiving collimated radiation and focussing same onto the sample surface,
 c. a detector for receiving radiation and converting same into an electrical signal,
 d. second optical means for collecting radiation reflected from the sample surface and focussing same onto the detector,
 e. means connected to the detector for pre-amplifying the electrical signal and for transmitting the electrical signal to a remote processing station.

13. The remote sampling terminal of claim 12, wherein the first optical means comprises a parabolic mirror, and the second optical means comprises a barrel ellipsoid mirror.

14. The remote sampling terminal of claim 13, further comprising means for sealing off from the outside atmosphere the regions within the terminal through which the radiation passes, and an optically-transparent window located to allow incident collimated radiation to be incident upon the first optical means.

15. The remote sampling terminal of claim 12 for diffuse reflectance analysis, wherein the sample support means is located to position the sample such that its sampling surface lies in a plane parallel to the incident collimated beam, the detector is located at a position facing and substantially opposite to the sample surface, and the first and second optical means are located substantially one behind the other and substantially in line with the incident collimated beam.

16. The terminal of claim 14, further comprising an enclosure having an outside wall with an opening for receiving the sample whereby the sample surface lies in the plane of the outside wall.

17. The terminal of claim 16, wherein one wall of the enclosure comprises a radiation transparent window.

18. The remote sampling terminal of claim 12, for external reflection analysis, further comprising a first plane mirror in the optical path between the first optical means and the sample surface, and at least a second plane mirror in the optical path between the second optical means and the detector.

19. The terminal of claim 18, further comprising an enclosure having an outside wall with an opening for receiving the sample whereby the sample surface lies in the plane of the outside wall.

20. The terminal of claim 19, wherein one wall of the enclosure comprises a radiation transparent window.

21. A remote sampling terminal for emission analysis, comprising:
 a. means for supporting a sample to be analyzed,
 b. means for controlling the temperature of the sample,
 c. means for collecting the radiation being emitted from a point of the sample and directing the same outside the terminal,
 d. said means for supporting a sample comprising an enclosure having an outside wall with an opening for receiving the sample whereby the sample surface lies in the plane of the outside wall.

22. The terminal of claim 21, wherein one wall of the enclosure comprises a radiation transparent window.

23. A remote sampling terminal for spectral analysis, comprising:
 a. means for supporting a sample to be analyzed,
 b. first optical means for receiving collimated radiation and focussing same onto the sample surface,
 c. a detector for receiving radiation and converting same into an electrical signal,
 d. second optical means for collecting radiation reflected from the sample surface and focussing same onto the detector,
 e. means connected to the detector for pre-amplifying the electrical signal and for transmitting the electrical signal to a remote processing station,
 f. means for varying the angle of incidence of the focussed radiation on the sample surface.

24. The remote sampling terminal of claim 23, wherein the first optical means comprises a parabolic mirror, and the second optical means comprises an ellipsoid mirror.

25. The remote sampling terminal of claim 24, further comprising means for sealing off from the outside atmosphere the regions within the terminal through which the radiation passes.

26. The remote sampling terminal of claim 23, further comprising means for independently varying the angle of reflection of the collected radiation from the sample.

27. The terminal of claim 26, further comprising a first support for the first optical means and a second support for the second optical means, and means for rotatably mounting the first and second supports for independent rotation about an axis through the sample.

28. The terminal of claim 27, further comprising means for housing the sample within an ambient-controllable chamber.

29. The terminal of claim 23, wherein the first optical means comprises a telescoping light pipe.

30. A remote sampling terminal for infrared emission analysis of a non-metallic sample, comprising:
 a. means for supporting the sample to be analyzed,
 b. means for controlling the temperature of the sample,
 c. means for collecting the radiation being emitted from a point of the sample and directing the same outside the terminal, said collecting and directing means comprising a curved mirror located in a position adjacent to the emitting surface of the sample, said curved mirror being configured to collect a substantial part of the emitted radiation and form therefrom a substantially collimated beam of radiation.

* * * * *